United States Patent [19]
Cheney

[11] 4,251,809
[45] Feb. 17, 1981

[54] METHOD AND APPARATUS FOR DETECTING THE PRESENCE OF WATER IN OIL

[75] Inventor: Oliver F. Cheney, Philadelphia, Pa.

[73] Assignee: Alco Standard Corporation, Valley Forge, Pa.

[21] Appl. No.: 12,959

[22] Filed: Feb. 16, 1979

[51] Int. Cl.³ ............................................. G08B 21/00
[52] U.S. Cl. ................................. 340/603; 73/61.1 R; 73/75; 324/65 P
[58] Field of Search ............................. 340/603, 540; 73/61.1 R, 75; 324/65 P

[56] References Cited

U.S. PATENT DOCUMENTS

| | | | |
|---|---|---|---|
| 1,836,316 | 12/1931 | Esau | 73/15 R |
| 2,571,470 | 10/1951 | Milligan | 73/61.1 R |
| 3,077,105 | 2/1963 | Ohlheiser | 73/61.1 R |
| 3,481,182 | 12/1969 | Lineberg | 73/61.1 R |
| 3,511,083 | 5/1970 | Reay et al. | 73/61.1 R |
| 3,695,095 | 10/1972 | Lineberg | 73/61.1 R |
| 3,796,089 | 3/1974 | Schuster et al. | 73/61.1 R |
| 3,926,038 | 12/1975 | Wunning et al. | 73/61.1 R |
| 4,112,744 | 9/1978 | Tassano | 73/61.1 R |
| 4,116,045 | 9/1978 | Potter | 73/61.1 R |
| 4,159,638 | 7/1979 | Potter | 73/61.1 R |

Primary Examiner—Glen R. Swann, III
Attorney, Agent, or Firm—Leydig, Voit, Osann, Mayer & Holt Ltd.

[57] ABSTRACT

A temperature sensitive resistor is immersed in a bath of quench oil and is supplied with electrical power sufficient to keep the resistor at a predetermined and substantially constant temperature above the vaporization point of water. When water is present in the oil, the water is vaporized by the resistor with the vaporization acting to cool the resistor and lower its resistance value. A signal which varies as a function of the drop in the resistance value of the resistor is produced and causes an increase in the power supplied to the resistor so as to keep the resistor at its predetermined temperature. In addition, transient pulses in the signal are detected and an alarm signal is produced when there is sufficient water present in the oil bath to cause the time-average value of the pulses to exceed a predetermined threshold. The resistor is protected from turbulence in the oil bath by a small chamber which contains a test sample of oil and which is periodically purged to bring a new test sample into the vicinity of the resistor and to allow the resistor to momentarily be exposed to air in order to clean slime and tar from the resistor.

22 Claims, 5 Drawing Figures

METHOD AND APPARATUS FOR DETECTING THE PRESENCE OF WATER IN OIL

BACKGROUND OF THE INVENTION

This invention relates to method and apparatus for detecting the presence of a predetermined concentration of one liquid such as water in another liquid such as oil. The oil may, for example, be a hot oil bath which is used for quenching workpieces after the workpieces have been heated in a heat treating furnace. A controlled atmosphere (e.g., a carbon enriched atmosphere) is sometimes maintained in the furnace in order to impart desirable characteristics to the workpieces during the heating process, and such atmosphere can exist above the oil bath.

The oil of a quenching bath is frequently flashed to high temperatures by the hot workpieces thus giving rise to the danger of an explosion resulting from minute amounts of water which, for various reasons, may be present in the oil. As the oil is heated, such water may vaporize and bubble to the surface. The steam bubbles carry with them small quantities of oil vapor which mixes with the atmosphere above the oil surface. The resulting oil vapor atmosphere is very combustible. To preclude the danger of explosion, the heat treating industry has determined that the oil should not contain more than 0.35 percent by volume of water.

Various systems have been devised for monitoring the moisture content of the oil and for producing an alarm signal when the moisture content exceeds an unsafe level. Many systems which have been used commercially, however, are unreliable and experience a relatively short service life. In many instances, such systems malfunction and fail to produce an alarm signal to warn the operating personnel that the water content has risen to a dangerous level. One of the possible causes resulting in a malfunction is that the sensing element for detecting the water becomes fouled by the oil and loses its sensitivity. Also, various additives and contaminants in the oil may cause the sensing element to produce a false signal or no signal at all. In some instances, the high temperature of the oil bath causes the sensing element to deteriorate. In still other instances, the sensing element must be re-conditioned for re-use once the element has been exposed to a high moisture content.

SUMMARY OF THE INVENTION

The general aim of the present invention is to provide a new and improved method and system for detecting and signaling the presence of minute quantities of water in oil, the invention being characterized by the utilization of a unique sensing element which is capable of functioning simply, reliably and with a comparatively long service life in various types of oil baths maintained at a wide range of temperatures.

A more detailed object of the invention is to achieve the foregoing by heating a temperature sensitive sensing element sufficiently to vaporize any water in the oil and by detecting and signaling a change in a characteristic of the sensing element when the latter changes in temperature as a result of the water vaporizing.

In even a more specific sense, the invention resides in the provision of a sensing element in the form of a temperature sensitive electrical resistor which is supplied with sufficient electrical power to cause heating of the resistor to a constant temperature above the vaporization point of water. When the resistor cools and drops in resistance value as a result of vaporization of water in the oil bath, a signal is produced and causes the power supplied to the resistor to increase so as to raise the resistor back to its original temperature. Transient pulses in the signal are detected and cause an alarm signal to be produced when there is sufficient moisture present in the oil to cause the time-average value of the pulses to exceed a predetermined threshold.

A further object of the invention is to prevent the sensing element from causing the alarm signal to be produced when the temperature of the oil bath itself changes and when the temperature of the sensing element is momentarily changed by various additives or contaminants which may be present in the oil.

An important object of the invention is to provide a system in which the sensing element maintains its sensitivity by periodically cleansing itself of tar or other oily residue which collects on the sensing element as a result of the latter being immersed in the oil bath.

The invention also resides in the novel manner in which the system operates to effect self-cleaning of the sensing element and to periodically draw a fresh supply of oil into the vicinity of the sensing element.

Still another object is to shield the sensing element from turbulence in the oil bath by enclosing the sensing element in a small chamber within the oil bath. Periodically, pressurized gas is introduced into the chamber to purge the oil from the chamber and momentarily allow the sensing element to be exposed to the gas for the purpose of effecting cleaning of the sensing element. The chamber thereafter is vented to enable a fresh sample of oil to flow into the chamber. The purging cycle is controlled to prevent the pressurized gas from significantly contaminating the atmosphere above the oil bath and, in addition, a warning signal is produced if the chamber fails to purge.

These and other objects and advantages of the invention will become more apparent from the following detailed description when taken in conjunction with the accompanying drawings.

DETAILED DESCRIPTION OF THE PREFERRED EMBODIMENT

Figure 1:
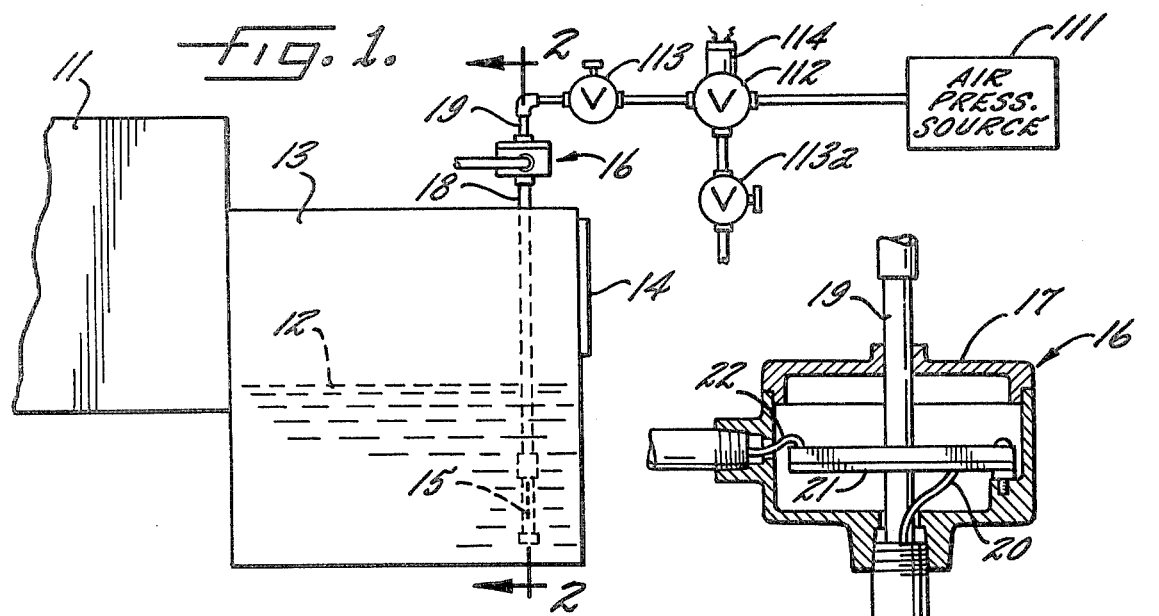
FIG. 1 is a side elevational view of a typical heat treating system equipped with new and improved water detecting apparatus incorporating the unique features of the present invention.

For purposes of illustration, the invention is shown in the drawings in conjunction with a heat treating furnace 11 in which workpieces (not shown) are heated to a very high temperature. An oil bath 12 contained in a closed cabinet 13 is positioned immediately adjacent the furnace for receiving and quenching the workpieces after they have been heated, the workpieces subsequently being removed through a door 14. A carbon enriched controlled atmosphere may be maintained in the furnace to impart certain metallurgical characteristics to the workpieces during the heat treating process. Since the cabinet communicates with the furnace, the same atmosphere usually exists in the cabinet.

While not shown, heaters are usually provided for maintaining the oil at a temperature which is typically 85 degrees C but which may range between 5 degrees and 230 degrees C. When hot workpieces are placed in the oil, localized parts of the bath 12 may flash to very high temperatures. To control the temperature of the bath, water may be circulated through cooling coils (not shown) in the bath and, as a result of condensation or leakage, the bath may become contaminated with water. As explained before, it is extremely important for safety reasons to constantly monitor the quenching oil bath and signal the presence of very minute quantities of water which may be present therein so precautionary steps can be taken to shut down the apparatus and remove such water.

Figure 3:
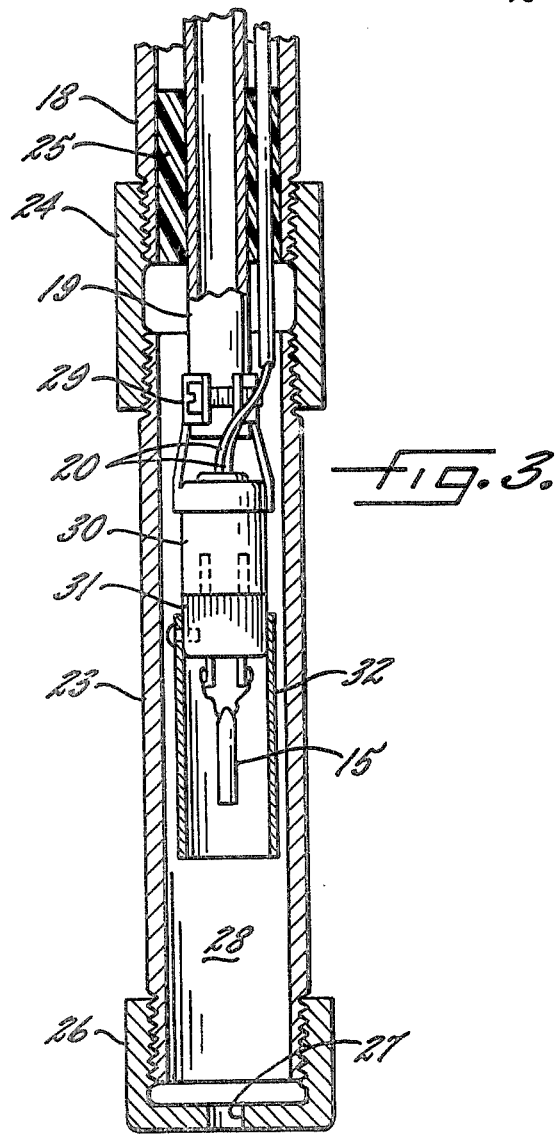
FIG. 3 is an enlarged fragmentary cross-sectional view taken substantially along the line 3—3 of FIG. 2.
Figure 2:
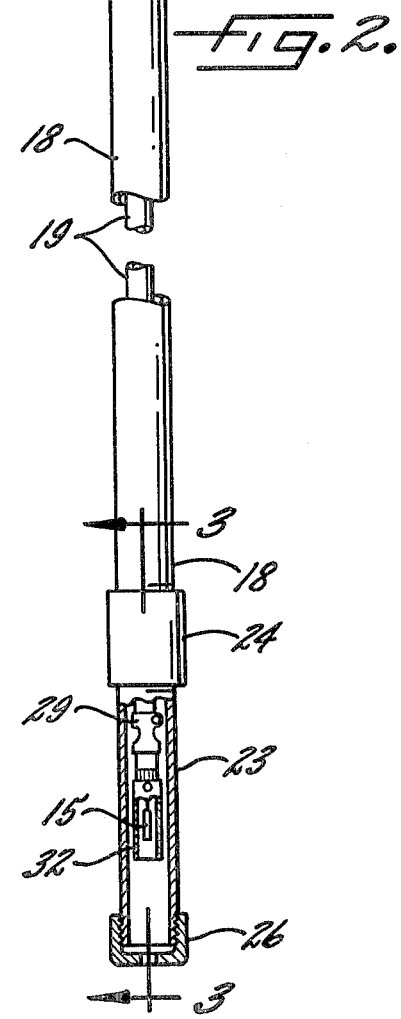
FIG. 2 is an enlarged fragmentary cross-sectional view of the detecting apparatus as taken substantially along the line 2—2 of FIG. 1.

The present system for monitoring the water content of the oil utilizes an electrical sensing element 15 which is adapted to be immersed in the oil bath. The sensing element is associated with a monitoring apparatus 16 supported on the oil bath cabinet 13 and having a housing 17 located above and outside of the cabinet. A long pipe 18 is threaded into the lower side of the housing and projects through an opening in the top of the cabinet and downwardly into the quenching oil. For a purpose to be explained subsequently, a copper tube 19 is disposed within the pipe 18 and projects through the housing 17, the lower end of the tube extending below the lower end of the pipe as shown in FIG. 3. Also, two insulated lead wires 20 extend downwardly through the pipe and alongside the tube and are connected at their upper ends to a printed circuit board 21 (FIG. 2) which is contained within the housing 17. Two wires 22 lead from the housing to a suitable power supply.

As shown in FIG. 3, the tube 19 and the wires 20 also extend into a short piece of pipe 23 which is connected to the lower end of the pipe 18 by a coupling 24. An epoxy block 25 is disposed in the lower end portion of the pipe 18 and establishes a seal between that pipe, the tube 19 and the wires 20 to prevent oil from rising into the pipe 18. The lower end of the pipe 23 is closed by a cap 26 having a vertical port or hole 27 drilled therethrough to permit oil from the bath to enter into the pipe 23. Thus, the pipe 23 defines a chamber 28 which communicates with the oil bath 12 via the hole 27 in the cap 26.

Disposed within the chamber 28 and clamped at 29 to the lower end of the tube 19 is a female plug 30 which is connected to the lower ends of the lead wires 20, the plug being positioned so as to leave the lower end of the tube open. The sensing element 15 is connected electrically to a male plug 31 which is coupled to the female plug and which is fastened to the upper end of a tubular sleeve 32 disposed within the chamber. The sleeve surrounds the sensing element and is open at its lower end to allow the oil in the chamber to come into contact with the sensing element.

In accordance with the present invention, the moisture sensing element 15 is in the form of a temperature sensitive resistor (i.e., a resistor whose resistance value changes as a function of its temperature) which is supplied with electrical energy at a rate which is controlled so as to normally heat the resistor to a predetermined constant temperature which is selected, in any event, to be above the vaporization point of water. When water is present in the oil, the individual water droplets come near to or in contact with the sensing resistor 15 and are heated above their boiling point. The latent heat of vaporization involved in exploding the droplets into steam extracts heat energy from the resistor so as to cool the resistor and lower its resistance value. Means are provided for detecting the drop in the resistance value of the resistor and for producing a signal for increasing the rate at which energy is supplied to the resistor so as to raise the resistor back to its original temperature. When the time-average value of transient pulses in the signal exceeds a predetermined threshold, an alarm signal is produced to warn the operating personnel that the water content of the oil bath is above a known safe level.

More specifically, the temperature sensitive resistor 15 herein is formed by wrapping several (e.g., 50) turns of fine platinum wire around a glass or ceramic substrate having a length of about 0.4" and a diameter of about 1/32". The ends of the platinum wire are connected electrically to the male plug 31 and thus the resistor is connected electrically to the circuit board 21 via that plug, the female plug 30 and the wires 20. The resistor has, for example, a resistance value of about 100 ohms at 0 degrees C.

Importantly, the platinum wire and the substrate of the resistor 15 are coated with tetrafluoroethylene (e.g., Teflon). As a result of the Teflon, the platinum wire and the substrate are protected from slime, tar, gunk and the like which may be present in the oil bath. Also, and as will be explained subsequently, the Teflon is important from the standpoint of the resistor maintaining its sensitivity.

Figure 4:
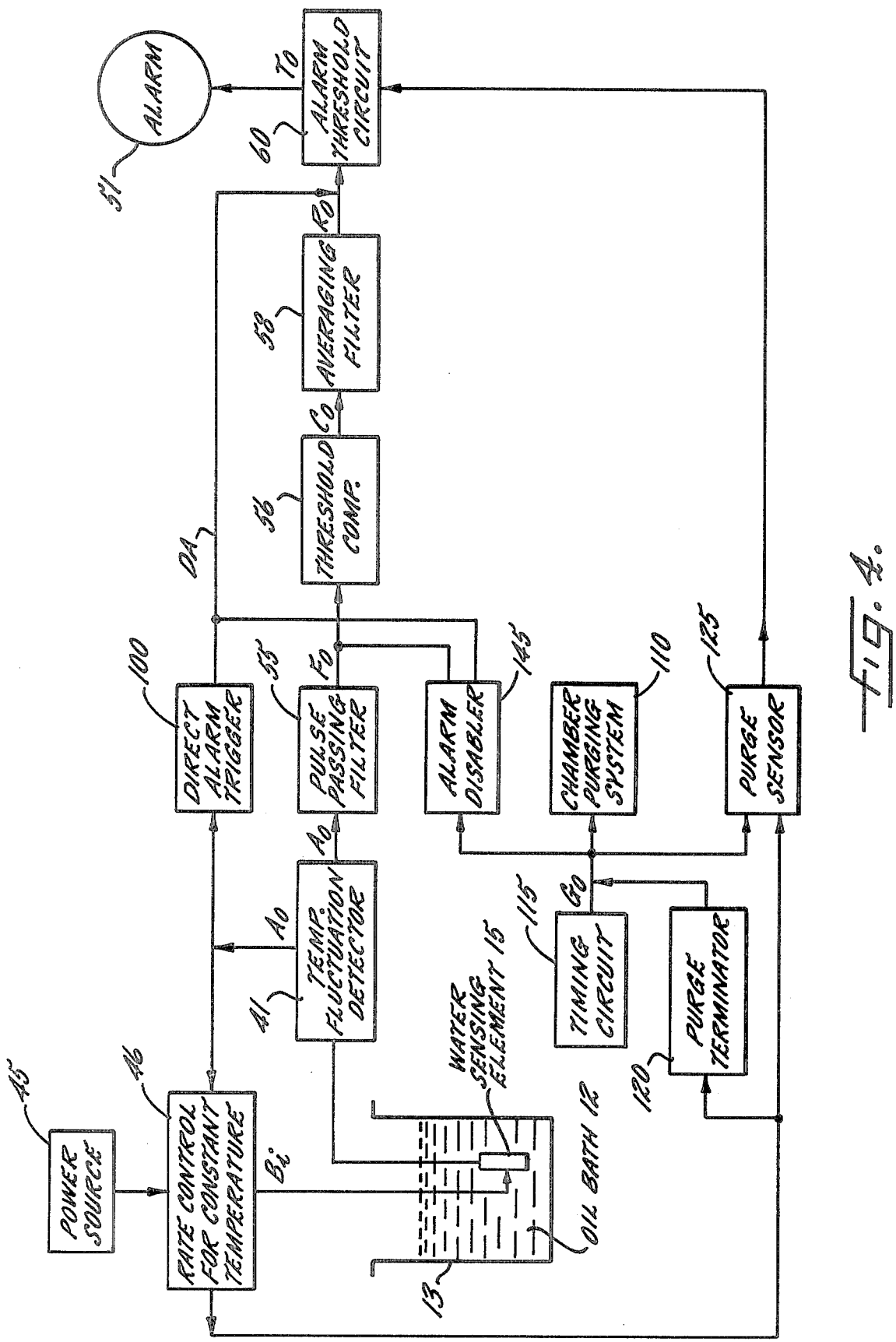
FIG. 4 is a general block diagram of the control for the detecting apparatus.
Figure 5:
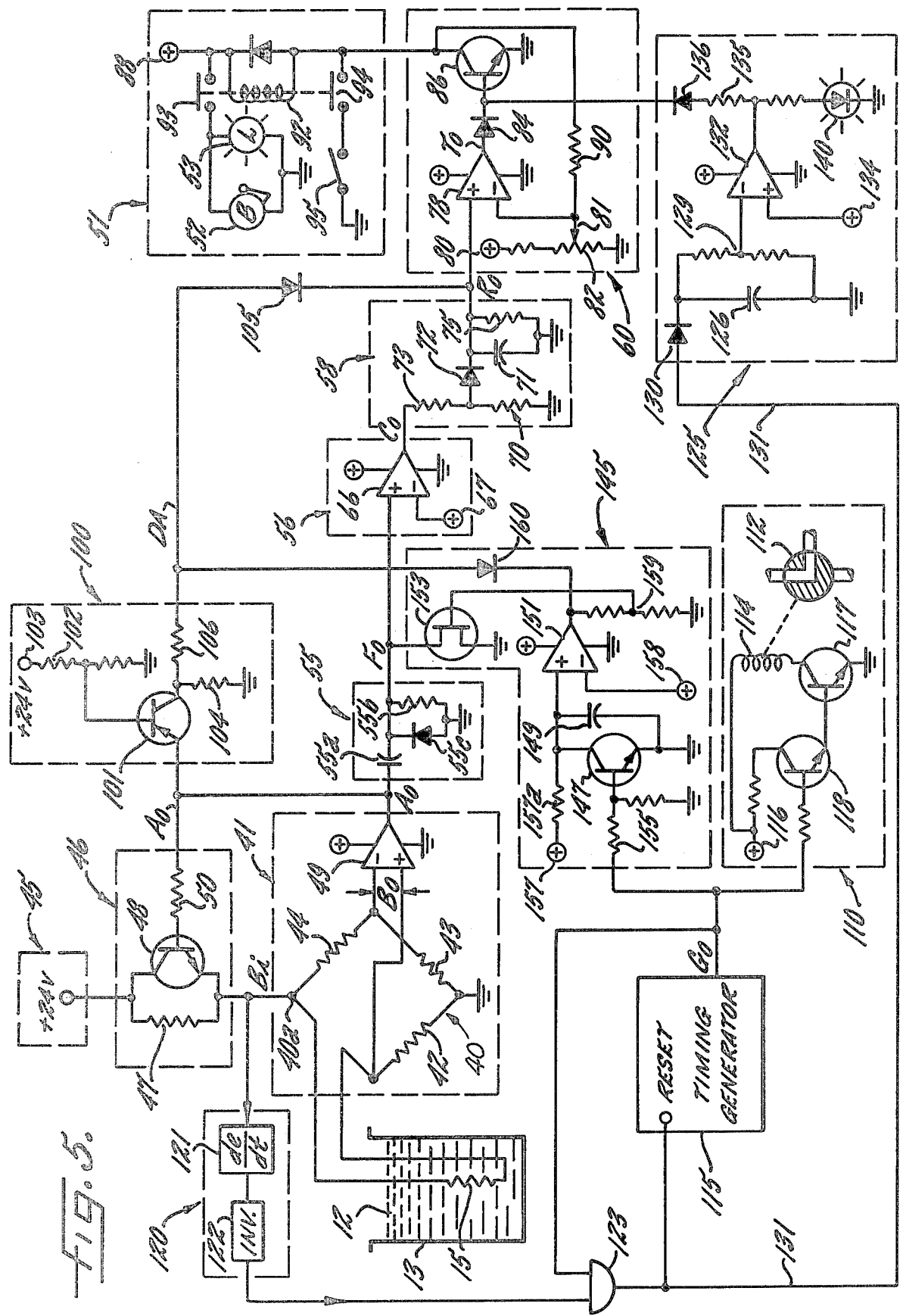
FIG. 5 is a schematic diagram of the electrical circuit of the control shown in FIG. 4.

A general block diagram of circuitry for controlling and responding to the temperature sensitive resistor 15 is shown in FIG. 4. A more specific diagram of typical circuitry is illustrated in FIG. 5. The circuitry of FIG. 5 may be incorporated in the printed circuit board 21.

In the preferred embodiment of the invention, the temperature sensitive resistor 15 forms the resistance in one branch of a Wheatstone bridge 40 (FIG. 5) which, in turn, forms part of a detector 41 (FIGS. 4 and 5) for sensing temperature fluctuations in the resistor. The three resistors 42, 43 and 44 in the other three branches of the bridge have known resistance values and have negligible temperature coefficients. The input terminals of the bridge are connected to an energy source 45 by way of a control 46 which regulates the rate at which energy is supplied, that is, the power supplied, to the resistor 15 in such a manner as to normally maintain the resistor substantially at some preselected temperature which is greater than the vaporization point of water but less than the vaporization point of the oil. By way of example, the resistor may be maintained at a preselected temperature of approximately 110 degrees C.

The energy source 45 preferably is a 24 volt direct current source. As shown in FIG. 5, the voltage source 45 is connected to the rate control 46 which here is formed by the parallel combination of a resistor 47 and an NPN transistor 48, the parallel combination being connected to the supply voltage input 40a of the bridge 40. Because of the voltage drop across the parallel combination, the input voltage to the bridge will always be less than 24 volts, but will decrease or increase as the collector-emitter path of the transistor becomes more or less conductive, i.e., exhibits a lesser or a greater resistance.

Connected across the output terminal of the bridge 40 is a differential amplifier 49 having very high open loop gain and forming part of the temperature fluctuation detector 41. The output of the amplifier is connected by way of a resistor 50 to the base of the transistor 48.

To facilitate an understanding of the invention as described thus far, let it be assumed that the sensing resistor 15 is immersed in a non-turbulent oil bath which is free of water and which is held at a fixed temperature, say, 85 degrees C. Let it be further assumed that the voltage $B_i$ which is being applied from the source 45 via the control 46 to the bridge input 40a is of such magnitude that current flowing through the bridge legs 15, 42 heats the resistor 15 to a steady state temperature of 110 degrees C. The transistor 48 is in a partially conductive state between cut-off and saturation, and preferably slightly above cut-off so that the voltage $B_i$ is substantially less than 24 volts. The temperature differential of 110 degrees −85 degrees =25 degrees is such that the rate of heat dissipated in the resistor 15 due to current flow just balances the rate of heat transfer by conduction to the oil. Finally, let it be assumed that the bridge is stabilized in steady state equilibrium (i.e., substantially balanced) and that the output voltage $B_o$ across the bridge is such that a slightly higher voltage is applied to the positive input terminal of the amplifier 49 than to the negative input terminal thereof. The resulting positive voltage output at $A_o$ supplies base-emitter current through the transistor 48 to make the collector-emitter path of the transistor slightly conductive.

Now let it be assumed that the oil bath drops to a slightly lower temperature (e.g., 75 degrees C.). The greater temperature differential increases the cooling of the sensing resistor 15. Because of its lower temperature, the resistor 15 drops in resistance and thus the bridge 40 becomes further unbalanced. Its output voltage $B_o$ changes to cause the voltage applied to the positive terminal of the amplifier 49 to increase relative to the voltage applied to the negative terminal thereof in proportion to the decreases in the resistance value of the resistor. As a result, the output voltage $A_o$ of the amplifier 49 increases proportionally (with a high gain factor) and in a positive sense. The higher voltage $A_o$ applied to the base of the transistor 48 increases the base-emitter junction current and decreases the collector-emitter resistance. This causes the input voltage $B_i$ to the bridge 40 to become higher and increase the power (that is, watts or the rate at which energy is transferred) supplied to the two parts (15, 42 and 44, 43) of the bridge. The rate of energy dissipated as heat in the sensing resistor 15 thus increases, and because the rate of heat energy lost by conduction to the oil tends to remain the same, the sensing resistor 15 rises in temperature and increases its resistance value. But as the resistor temperature rises, the rate of heat energy loss to the oil increases, until heat input rate matches heat loss rate. When the resistor is heated back substantially to its original temperature, and assuming that the oil bath is still at its lower temperature (75 degrees C.), the bridge reaches steady state equilibrium but stabilizes with offset (i.e., the bridge output voltage $B_o$ is very slightly higher than its original value) so that the input voltage $B_i$ is maintained sufficiently high to hold the resistor substantially at its original temperature.

The input voltage $B_i$ to the bridge 40 is modified similarly but reversely when the temperature of the oil bath increases and causes the temperature and resistance value of the sensing resistor 15 initially to increase. That is, the output voltages $B_o$ and $A_o$ of the bridge 40 and the amplifier 49, respectively, become less positive to increase the collector-emitter resistance of the transistor 48 and reduce the input voltage $B_i$ to the bridge thereby to lower the temperature of the sensing resistor 15. In this way, the resistor is maintained at a substantially constant steady-state temperature regardless of the temperature of the oil bath. Generally stated, the rate of electrically supplied energy input to the resistor 15, the value of the bridge output voltage $B_o$, and the value of the bridge input voltage $B_i$ will all vary as inverse monotonic functions of the oil bath temperature; it is unimportant if, as here, the relationship is non-linear.

It should also be noted that the steady-state temperature of the sensing resistor 15 will be held substantially constant regardless of the thermal conductivity of the oil bath in which the resistor is immersed. If for some reason the heat conductivity of the oil increases to create comparatively faster cooling of the resistor, the input voltage $B_i$ to the bridge will be increased. On the other hand, the input $B_i$ will be of a lower value when the resistor is immersed in a bath of lower thermal conductivity.

Now let it be assumed that the oil bath 12 is contaminated with a quantity of water. Any water droplets in the vicinity of the sensing resistor 15 will be heated and vaporized by the resistor, which is residing at a predetermined high temperature, here assumed to be 110 degrees C. As each water droplet vaporizes into steam, it extracts heat energy from the resistor and causes the temperature of the latter to drop momentarily. That is, as the temperature of the resistor 15 initially falls, the bridge output voltage $B_o$ rises, resulting in a tendency of the bridge input voltage $B_i$ to rise; but after the water droplet has been fully vaporized and oil again surrounds the resistor 15, the bridge output $B_o$ and the input voltage $B_i$ return to their original values. Thus, a voltage pulse $B_o$ which increases in a positive sense will appear at the output terminals of the bridge 40 each time a water droplet explodes into steam and lowers the temperature and resistance value of the resistor. Viewed in a temporary or transient sense, the flashing of each water droplet produces an amplified voltage pulse $A_o$ at the output of the amplifier 49. This pulse is applied to the transistor 48 to increase and then restore the input voltage $B_i$ to the bridge, thereby tending to increase and then restore the temperature of the resistor 15. The pulses $B_o$ and $A_o$ vary in magnitude and duration (i.e., area or volt-seconds) in accordance with the size of a given water droplet which is vaporized and they vary in frequency in accordance with the number of droplets which are vaporized in a given period of time.

In carrying out the invention, the transient output pulses $A_o$ from the amplifier 49 are detected and averaged. When the average value of those pulses (which is proportional to the area and frequency thereof) exceeds a predetermined threshold, a warning signal is produced to indicate that the moisture content of the oil exceeds some selected concentration level. For these purposes, provision is made of an alarm 51 which herein consists of a bell 52 (FIG. 5) and an indicating light 53. The alarm is responsive to the output signal $A_o$ of the amplifier 49 but means are provided for preventing the alarm from being triggered and producing the warning signal when the output signal $A_o$ is of constant magnitude (lacking in transient pulses) or when the output signal $A_o$ contains transients or pulses as a result of factors other than a high water content.

In the present instance, these means comprise, first, a filter or differentiator 55 (FIGS. 4 and 5) which responds to the output voltage $A_o$ of the amplifier 49 and which passes output pulses $F_o$ only when the output voltage $A_o$ contains a positive-going transient pulse, the filter thereby preventing the alarm 51 from responding to any slow change, whether temporary or permanent, in the output voltage $A_o$. As will become apparent, this prevents the alarm from responding to gradual changes in the voltage $A_o$ caused by variations in the temperature or conductivity of the oil bath itself. Secondly, a threshold, saturating comparator 56 responsive to the output of the filter 55 serves to block low amplitude "noise" which might appear in the output pulses $F_o$ so as to prevent the alarm from responding to spurious variations in the output pulses of the filter. The comparator also converts each input pulse $F_o$ which exceeds a predetermined amplitude into an output pulse $C_o$ of fixed amplitude, but of width generally proportional to the width of the corresponding input pulse. Thirdly, an averaging filter or integrator 58 responsive to the output pulses $C_o$ of the comparator 56 converts the pulses $C_o$ into a dc. voltage signal $R_o$ whose magnitude varies as a generally proportional function of the short term time average (frequency and width) of the pulses $C_o$. Fourthly, an alarm threshold circuit 60 produces an output signal $T_o$ to trigger the alarm 51 only when magnitude of the signal $R_o$ from the averaging filter 58 exceeds a predetermined (but adjustable) threshold value.

Considering FIG. 5 in more detail, the pulse passing filter 55 is in the form of a clipping differentiator and comprises a capacitor 55a connected to be charged when positive-going increases in the voltage $A_o$ produce current flow through a resistor 55b, the resulting voltage drop creating a positive pulse at $F_o$. Negative-going changes in the voltage $A_o$ result in capacitor charging current flowing in the opposite direction, but such current is shunted forwardly through a diode 55c, producing negligible voltage drop thereacross, so that negative pulses are clipped or eliminated from the filter output signals at $F_o$.

The comparator 56 is here shown as a high gain operational amplifier 66 (FIG. 5) connected without feedback and operated in a saturated mode so that it functions as a voltage comparator. Of course, known alternatives such as a Schmitt trigger circuit may be used. The output of the filter 55 is connected to the positive or non-inverting input terminal of the amplifier 66 while the negative or inverting input terminal is connected to reference voltage source 67 which is maintained, for example, at about 8.5 volts. As long as the magnitude of a voltage pulse $F_o$ from the filter 55 is below this voltage threshold, the amplifier 66 output $C_o$ remains zero. When, however, a pulse $F_o$ exceeds the selected threshold, the amplifier immediately saturates to produce its maximum positive output, i.e., a square pulse $C_o$ of 20 volts, for example. The output pulses $C_o$ from the amplifier 66 are of constant height and of differing width with the width of each pulse varying according to the duration of a pulse $F_o$ produced as a result of a vaporizing water droplet. The pulses $C_o$ vary in frequency according to the number of water droplets which are vaporized in a given period of time.

In many instances, the oil bath 12 may include an additive employed to impart special quenching characteristics. The additive may not be completely miscible with the oil and may exist in the form of globules. The globules formed by the additive may be of higher heat conductivity than the quenching oil and, as they come in contact with the sensing resistor 15, may produce momentary cooling effects—but not as great as that produced by vaporization of water droplets. Thus, the globules may cause voltage pulses $F_o$ of relatively small magnitude to appear at the output of the filter 55. Because of the threshold comparator and amplifer 66, however, such low level pulses are masked and are not effective to cause triggering of the alarm 51. The amplifier also serves to mask low level pulses $F_o$ which might be produced by any convection currents in the chamber 28, such convection currents serving to cool the resistor 15. In summary, the threshold comparator eliminates spurious responses to low level noise or side effects, and causes the pulses to reflect the presence of the more highly volatile bath constituent of interest, here water.

The averaging filter 58 converts the pulses $C_o$ into a dc. voltage $R_o$ which varies substantially in proportion to the time-averaged value of such pulses. Because the widths of transient pulses at $A_o$, and the frequency of such pulses, are directly related to the size and the concentration of the vaporized water droplets, the averaging results in the voltage $R_o$ being generally a measure of the percentage of water in the oil bath. Herein, the filter is preceeded by a voltage divider 70 connected to the output of the amplifier 66 and connected to a capacitor 71 by way of an isolating diode 72. Each positive pulse $C_o$ tends to charge the capacitor by current flow through the resistor 73 of the divider, the capacitor thereby accumulating a charge to create voltage $R_o$. During those intervals, however, between the successive pulses $C_o$, the capacitor discharges through a parallel resistor 75, so that the capacitor voltage $R_o$ exponentially decays. The charging time constant established by the resistor 73 of the voltage divider 70 and the capacitor 71 is chosen such that it is low in comparison to the discharging time constant established by the resistor 75 and the capacitor 71. That is, the resistance value of the resistor 73 is considerably less than that of the resistor 75. As is well known, those time constants are selected to make ripples in the voltage $R_o$ inconsequential, and the filter 58, or what is commonly called an R-C integrator, serves to make the voltage $R_o$ substantially proportional to average volt-seconds of the pulses $C_o$.

The alarm threshold device 60 is here formed by a high gain operational amplifier 78 (FIG. 5) whose non-inverting input terminal receives the output $R_o$ of the filter 58. The inverting input terminal of the amplifier is connected to a voltage source 80 by way of a voltage divider 82 and is biased at a predetermined threshold reference voltage (e.g., 3 volts). The reference is adjustable by setting a wiper 81 associated with the divider. As long as the signal $R_o$ from the filter 58 remains below the threshold voltage, the output signal $T_o$ remains at zero. Any time the voltage $R_o$ exceeds the threshold level, however, the amplifier saturates and produces a positive signal $T_o$. This signal is applied by way of an isolating diode 84 to the base of a grounded-emitter NPN transistor 86 to bias the transistor to "full on" and allow collector-emitter current to flow from a source 88 of positive voltage through a series connected relay coil 92. When transistor 86 is cut-off (in the absence of a positive voltage at $T_o$) trickle current flows through the coil 92, a resistor 90 and the lower portion of the voltage divider 82, thereby making the reference voltage at wiper 81 have a relatively high preselected value. But when transistor 86 is turned on, its collector-emitter path shunts such current to ground so that the reference voltage decreases. This feedback action tends to "latch" the transistor 86 in the full on state; that is once it turns on and energizes the relay coil 92, it will stay on even if the voltage $T_o$ thereafter falls somewhat.

When the relay coil 92 is energized, as explained above, it closes contacts 93 to energize the warning bell 52 and the warning light 53, the latter being connected in parallel to the voltage source 88 via those contacts. Energization of the relay coil 92 also closes relay contacts 94 which establish a sealing circuit through a normally closed manual reset switch 95 to keep the coil energized. The bell 52 and the light 53 of the alarm 51 thus will remain energized until the switch 95 is opened manually to de-energize the relay coil.

From the foregoing, it will be apparent that the pulse passing filter 55 prevents the alarm 51 from being triggered by the output voltage $B_o$ per se of the bridge 40 and prevents the alarm from responding to very gradual changes in the output voltage $B_o$. The comparator 56 blocks low-level output pulses $F_o$ from the filter 55 so that "noise" or spurious pulses caused by additives or the like are masked and are not effective to trigger the alarm. The averaging filter 58 smooths the output pulses $C_o$ from the comparator and produces a dc. voltage $R_o$ which varies generally in proportion to the percentage of water in the oil bath. Finally, the threshold device 60 triggers the alarm only when the output signal $R_o$ from the averaging filter exceeds a predetermined threshold selected by adjusting the wiper 81 and chosen to correspond to a known "safe" water percentage in the oil bath. Thus, the alarm will not be triggered if the water content of the oil is low and small water droplets are only infrequently vaporized by the sensing resistor 15.

As a fail-safe measure, the alarm 51 will, under certain circumstances, be triggered directly in response to the output voltage $A_o$ of the differential amplifier 49. Such direct triggering is effected when the output voltage $A_o$ of the amplifier rises to such a high value that the voltage applied to the transistor 48 causes the input voltage $B_i$ to the bridge 40 to approach the maximum possible value (for example, almost 24 volts when transistor 48 is fully on, in view of the source 45 being 24 volts). The voltage $B_i$ could, for example, approach 24 volts if the oil bath 12 is at a very low temperature, if additives or contaminants in the oil are of high conductivity and effect abnormal cooling of the sensing resistor 15, or if the water content of the oil is extremely high and effects continuous cooling of the resistor rather than pulsed cooling.

If the input voltage $B_i$ to the bridge 40 approaches 24 volts, a potentially unsafe condition could exist since the output voltage $B_o$ of the bridge would only change unidirectionally and would not pulsate with further cooling of the resistor 15 caused by vaporization of water droplets. Thus, pulses $F_o$ would not be passed by the filter 55 and the alarm 51 would not be triggered even though there existed an unsafe water concentration in the oil bath.

To guard against such a condition, means 100 are provided for triggering the alarm 51 directly when the output voltage $A_o$ of the amplifier 49 rises so high as to cause the bridge input voltage $B_i$ to exceed a predetermined threshold which is somewhat less than its maximum possible value, i.e., 24 volts. Herein, the direct alarm trigger 100 comprises a PNP transistor 101 (FIG. 5) whose emitter is connected to receive the output signal $A_o$ from the differential amplifier 49. The base of the transistor is connected to a reference supply voltage from a voltage divider 102 energized from a voltage source 103, while the collector of the transistor is connected via a load resistor 104 to ground. An output signal DA (normally zero volts) is taken via a current limiting resistor 106 and an isoltating diode 105 to the non-inverting input terminal of the operational amplifier 78.

Assuming that the threshold or reference voltage from the divider 102 is +23 volts, the transistor 101 will be cut-off and the output signal DA will be zero volts unless and until the signal at $A_o$ rises above approximately +23.5 volts. When the latter occurs (and the bridge input voltage $B_i$ is about 22 volts), the emitter-collector path of the transistor 101 becomes conductive and current flow through the load resistor 104 to make the output signal DA have a relatively high positive value which changes the capacitor 71 to a voltage which exceeds the reference voltage at wiper 81. Accordingly, the amplifier 78 is driven to saturation and the relay coil 92 is energized to actuate the alarm 51 (as previously explained)—even though the output signal $C_o$ from comparator 56 is insufficient in itself to cause the alarm to be actuated.

It will be noted that the sensing resistor 15 is shielded within the chamber 28 by the pipe 23 and the cap 26 (FIG. 3) and thus is protected from any turbulence which might be present in the oil bath. Such protection is desirable since any substantial movement of oil past the resistor would increase the cooling effect of the oil and could result in a false alarm signal being created. Because the sensing resistor is, however, substantially isolated from the main body of the oil bath, it is important that a fresh supply of oil be brought periodically into contact with the resistor in order to insure that the oil which is being monitored by the resistor is a representative sample of the main bath.

In furtherance of the invention, the chamber 28 is periodically purged of oil, the purging serving two important purposes. First, the purging removes the previously monitored oil from the chamber and causes a new sample of oil to be brought into the vicinity of the sensing resistor 15. Secondly, the sensing resistor is momentarily exposed to air during the purging cycle. For reasons which are not fully understood, exposure of the resistor to air causes the outer Teflon coating of the resistor to cleanse itself of slime, tar or other contaminants which may have gathered on the coating while the resistor was immersed in oil. Accordingly, a buildup of contaminants on the resistor is avoided and thus the resistor maintains its sensitivity since the thermal insulating effect which otherwise would be created by an accumulation of contaminants is avoided. If the resistor became heavily coated with contaminants, its surface might be insulated from the oil bath and the latter might not be heated to a sufficiently high temperature to vaporize water droplets, or at least the calibration of the system might be undesirably changed.

Purging of the chamber 28 is effected by means of a purging system 110 which periodically introduces compressed air into the copper tube 19 to drive oil down and out of the chamber through the hole 27 in the cap 26. Thus, the upper end of the copper tube communicates with a source 111 (FIG. 1) of compressed air by way of a two-position, three-way valve 112 and an adjustable needle valve 113 for regulating the rate of air flow from the three-way valve to the tube. The three-way valve is adapted to be shifted between its positions by a solenoid 114. When the solenoid is energized, communication is established between the pressurized air source and the tube 19 to force oil out of the chamber. When the solenoid is de-energized, the chamber 28 and the tube 19 are vented to atmosphere through the valve 112 and an exhaust line to enable a fresh charge of oil to flow up and into the chamber through the hole 27 in the cap 26. An adjustable needle valve 113a in the exhaust line controls the rate of flow therethrough.

The valve 112 is normally held in its vent position and is automatically shifted to its purge position and then back to its vent position at periodic intervals. This is achieved through the use of a timing circuit 115 for controlling energization and de-energization of the solenoid 114 which effects shifting of the valve. While various forms of timers may be used, the present timing circuit employs a free-running but resettable square wave generator capable of producing a repeating voltage signal $G_o$ which, as long as the generator is not reset, jumps to and remains at a high level (e.g., +20 volts) for a predetermined interval and then falls to and remains at a low level (e.g., zero volts) for a certain interval before returning to the high level. By way of example, the high level signal may have a duration of 8 seconds while the low level signal may have a duration of 52 seconds, providing a total cycle period of 60 seconds.

The solenoid 114 for the valve 112 is energized to shift the valve to its purge position when the output signal $G_o$ from the timing generator 115 is high and is de-energized to shift the valve to its vent position when that output is low. For this purpose, the solenoid is connected in series with a voltage source 116 (FIG. 5) and the collector of a NPN transistor 117 whose base is connected to the emitter of a second NPN transistor 118, the two transistors forming a Darlington pair which functions as a single transistor operative with a smaller range of input base current values. The collector of the transistor 117 is coupled to the voltage source 116 and its base is coupled to the output of the timing generator 115.

When the output signal $G_o$ of the timing generator 115 is at a high level, the transistor 118 is turned on to allow current to flow from the source 116 to the base of the transistor 117 to turn the latter on. This permits current to flow through the solenoid 114 to energize the solenoid and effect shifting of the valve 112 to its purge position. When the output signal $G_o$ goes low, both transistors are cut off to interrupt the flow of current through the solenoid and to cause the valve to shift to its vent position.

If the valve 112 is in its purge position for eight seconds, the volume of compressed air introduced into the chamber 28 is sufficient to completely empty the chamber of oil. It is desirable that the chamber be substantially emptied and that the sensing resistor 15 be exposed to air for a short period of time so that the resistor can cleanse itself. It is undesirable, however, to completely empty the chamber of oil for as long as one second since this would allow a significant amount of air to escape from the chamber through the hole 27 in the cap 26 and to enter the cabinet 13. Any escaping air would mix with the controlled atmosphere being maintained in the furnace 11 and could detrimentally affect the integrity of the controlled atmoshpere.

Accordingly, provision is made to shift the three-way valve 112 to its vent position after the oil level in the chamber 28 drops below the lower end of the sensing resistor 15 but before the oil is pushed to the level of the hole 27 and the chamber is completely emptied of oil. This is achieved with a purge terminator 120 which produces a signal when the sensing resistor tends to attain a temperature elevated above its nominal preselected constant temperature as a result of being exposed to air. Such signal is used to reset the timing generator 115 to switch the output signal $G_o$ to a low level and thereby de-energize the solenoid 114 to shift the valve 112 to its vent position.

More particularly, the signal for resetting the timing generator 115 is produced by sensing the input voltage $B_i$ to the bridge 40. When the purging cycle begins, oil in the chamber 28 flows downwardly past the sensing resistor 15. Just the flowing of oil removes heat at a faster rate and tends to drop the temperature of the resistor. The inverse cooling effect produced by movement of the oil causes the input voltage $B_i$ to the bridge to rise. But, as the oil falls and exposes the resistor 15 to air, the rate of heat transfer from the resistor decreases and its temperature tends to rise quickly. It rises above the selected nominal constant temperature. Accordingly, the closed loop action of the bridge 40, amplifier 49, and transister 48 causes the input voltage $B_i$ to drop sharply.

When the input voltage $B_i$ to the bridge 40 undergoes a sharp drop, a differentiator 121 (FIG. 5) of well known construction operates in a conventional manner to produce a negative-going output pulse. A conventional inverter 122 converts the pulse into a positive going pulse which is applied to one input terminal of an AND gate 123. The other input terminal of the gate is coupled to the output of the timing generator 115. The output terminal of the gate is coupled to the reset terminal of the generator.

If a positive going pulse is applied to the AND gate 123 at any time while the output signal $G_o$ of the timing generator 115 is at a high level, the gate will pass the pulse to the reset terminal of the generator. The pulse will immediately reset the generator to cause its output signal to go low and cause the chamber 28 to be vented to atmosphere for a period of 52 seconds.

In operation, therefore, after the valve 112 is shifted to its vent position, oil will continue to flow from the chamber for a very short time (and at a rate determined by the needle valves 113 and 113a) until the chamber 28 and the tube 19 are fully vented. While a small and insignificant volume of air may escape from the chamber during the continued flow, such flow insures that the oil will indeed fall below the extreme lower end portion of the resistor and allow that portion of the resistor to self-clean.

From the foregoing, it will be apparent that the timing signal $G_o$ from the generator 115 provides a sufficient interval for oil to drop below the sensing resistor 15 and for a substantial quantity of oil to flow from the chamber 28 so as to insure that the resistor will be momentarily exposed to air and also to insure that a representative sample of fresh oil will flow back into the chamber after the purging cycle has been completed. The purging cycle is automatically terminated, however, by automatic resetting of the timing generator (and switching of the signal $G_o$ to its low value) when the oil drops below the resistor and before or just after all of the oil is driven out of the chamber so that no significant amount of air is allowed to escape into the cabinet 13. Because the termination of the purging cycle is not dependent on a time function, the system operates reliably with oils of various viscosities and in baths of various depths.

As pointed out above, it is important that the chamber 28 be periodically purged so that the sensing resistor 15 monitors successive fresh and representative samples of the oil bath. Various malfunctions in the compressed air system could, however, result in a failure to purge. For example, the air supply from the pressurized source 111 could be lost, the three-way valve 112, the needle valves 113 and 113a or the hole 27 in the cap 26 could become clogged with foreign material, or the solenoid 114 could fail. In any of these cases, purging of the chamber 28 might not be achieved and thus the sensing resistor 15 could be continuously monitoring the same sample of oil and providing a safe indication after the moisture content of the main oil bath 12 had, for some reason, increased to an unsafe percentage.

To avoid such a situation, provision is made to detect purging of the chamber 28 and to trigger the alarm 51 if no purging occurs within a predetermined time span. For this purpose, a purge cycle failure sensor 125 comprises an R-C integrator having a capacitor 126 (FIG. 5) adapted to be charged with a low time constant from source 131 via a diode 130 and adpated to discharge through a divider 129 having a very large resistance value. The diode 130 is controlled (via line 131) by the output from the AND gate 123 so that it conducts and the capacitor 126 is charged each time (normally about every 60 seconds) the sensing resistor 15 is exposed to air. The output voltage of the capacitor is applied to the inverting input terminal of an operational amplifier 132 whose non-inverting terminal is biased by a source 134 of positive reference voltage of relatively low magnitude such as, for example, 2.4 volts. The output of the amplifier is coupled by way of a current limiting resistor 135 and an isolating diode 136 to the base of the drive transistor 86 for the alarm 51.

When the chamber 28 is being periodically purged in a normal manner, the AND gate 123 passes pulses at regular intervals as the input voltage $B_i$ to the bridge 40 falls after the oil flows downwardly past the sensing resistor 15 and exposes the resistor 15 to air. Each time a pulse is transmitted by the AND gate 123, the diode 130 momentarily conducts to cause substantially full charging of the capacitor 126 from the pulse source 131. When the pulse from the AND gate disappears, the capacitor begins discharging with a long time constant. If charging reoccurs within a predetermined time span (e.g., 10 minutes), the voltage on capacitor 126 never falls below the magnitude of the reference voltage 134, and the output of amplifier 132 will remain at zero volts. If a predetermined number of cycle periods (say, ten) occur without the capacitor 126 being re-charged, however, the output of amplifier will swing positive, turn on transistor 86 and cause the relay 92, 93, 94 to pick up and seal in. The alarm will be activated to apprise an attendant of the purging malfunction. Preferably, the nature of the malfunction is indicated by a light emitting diode 140 which is activated by a positive voltage at the output of amplifier 132.

As stated previously, the rate of heat energy removal from the sensing resistor 15 increases when oil flows downwardly past the resistor during the purge cycle. The resistor temperature initially falls, but as the resistor becomes exposed to air (reducing the rate of heat energy removal) its temperature then rises. When oil thereafter flows back into the chamber 28 and upwardly past the resistor as the purge cycle ends, the resistor temperature again falls. As a consequence of each such falling in the sensing resistor temperature, the output voltage $B_o$ of the bridge 40 increases sharply and could result in the alarm 51 being triggered, either (i) by way of the pulse passing filter 55 and comparator 56 or (ii) by way of the direct alarm trigger 100 if the output voltage rises sufficiently to cause the voltage $A_o$ to exceed momentarily the threshold which will turn on the transistor 101.

To prevent the alarm 51 from being thus triggered falsely during the purge cycle, means 145 are provided for disabling the alarm, not only during the actual purge when valve solenoid 114 is energized but also for a short time after the chamber 28 has been vented and while oil is flowing back into the chamber and is cooling the sensing resistor 15. The disabling means 145 respond to the output of the timing generator 115 and comprise a grounded-emitter NPN transistor 147 (FIG. 5), a capacitor 149, an operational amplifier 151 and a bipolar field effect transistor (FET) 153.

The base of the transistor 147 is coupled to the output of the timing generator 115 by way of a voltage divider 155 while the collector of the transistor is connected to a source 157 of positive voltage. The capacitor 149 is connected across the collector and emitter of the transistor with that collector being connected to the non-inverting input terminal of the operational amplifier 151. The inverting terminal of that amplifier is biased by a positive source 158 of reference voltage of, for example, 15 volts. The output signal of the amplifier is picked off from a voltage divider 159 and is supplied to the gate electrode of the FET 153. The source electrode of the FET is coupled to the output of the pulse passing filter 55 while the drain electrode is connected to ground.

When the output signal $G_o$ of the timing generator 115 is at a low level (as is the case during 52 second intervals when oil is being tested) the transistor 147 is cut off. Assuming that capacitor 149 has been charged via a collector resistor 157a, a high positive voltage is applied to the non-inverting terminal of the amplifier 151.

In consequence, the voltage applied to the non-inverting terminal of the amplifier 151 is greater than that applied to the inverting terminal by the reference source 158 and thus the output signal of the amplifier normally resides at a high level. That signal keeps the gate electrode of the FET 153 positive relative to ground so that a very high resistance conduction path exists between the source and drain electrodes. The FET 153 thus does not shunt the pulses $F_o$ and the system operates in the manner previously described.

When the output signal $G_o$ of the timing generator 115 switches to a high level at the start of the 8 second purging interval, the transistor 147 is turned on. The capacitor 149 quickly discharges through the collector-emitter path of transistor 147, and the voltage drop across resistor 157a reduces the signal at the non-inverting terminal of the amplifier 151 below the reference voltage at 158. The output of the amplifier thus switches to a negative level to apply a negative potential to the gate electrode of the FET 153, making the source-drain path fully conductive. Accordingly, the output signal $F_o$ of the filter is shorted to ground during the eight second purging interval, thereby to prevent such signal from triggering the alarm 51. When the eight second interval ends, the timing signal $G_o$ swings low, transistor 147 cuts off, and capacitor 149 begins charging through the resistor 157a. A finite time is thus required before the voltage at the non-inverting input of amplifier 151 rises above the reference voltage at 158, so that the normal operation of the circuitry (comparator 56 responsive to pulses $F_o$) is inhibited for a few seconds into the 52 second "low" interval of the timing signal $G_o$.

The output of the amplifier 151 also is connected to the collector of the transistor 101 by way of a diode 160 which is poled as shown in FIG. 5. When the output signal of the amplifier 151 goes negative at the start of each eight second purging cycle, current is drawn from ground through resistors 104, 106 and diode 160. The signal DA is thus clamped to a negative level (despite any attempted conduction by transistor 101) and therefore no conduction by diode 105 can occur—during the purge interval or shortly thereafter—to initiate a "direct alarm" action.

I claim:

1. A method for signaling the presence of a predetermined concentration of water in oil, said method comprising the steps of, placing a temperature sensitive electrical resistor in contact with said oil, supplying electrical power to said resistor to heat the resistor to a temperature above the vaporization point of water and below the vaporization point of said oil, producing a signal which varies as a function of the resistance of said resistor, detecting transient pulses produced in said signal when the resistor changes temperature in response to the vaporization of water adjacent the resistor, and producing an output signal when the time-average value of said pulses exceeds a predetermined threshold.

2. A method for signaling the presence of a predetermined concentration of water in a bath of oil, said method comprising the steps of, placing a temperature sensitive electrical resistor in contact with said oil, supplying electrical power to said resistor to heat the resistor to a predetermined temperature value above the vaporization point of water and below the vaporization point of said oil, producing a signal which varies as a function of the resistance of said resistor, increasing or decreasing the power supplied to said resistor in response to changes in said signal resulting from decreases or increases, respectively, in the resistance of said resistor thereby to maintain the steady state temperature of said resistor substantially at said predetermined value, detecting transient pulses produced in said signal when said resistor cools and drops in resistance value in response to the vaporization of water adjacent the resistor, and producing an output signal when the time-average value of said pulses exceeds a predetermined threshold.

3. A method as defined in claim 2 in which said resistor is disposed within a chamber located in and communicating with said bath and normally containing oil, said method further comprising the steps of periodically causing oil to flow out of said chamber and into said bath and thereafter causing oil to flow from said bath and into said chamber.

4. A method as defined in claim 3 further including the step of stopping the flow of oil out of said chamber before said chamber is completely empty of oil.

5. A method as defined in claim 3 further including the step of stopping the flow of oil out of said chamber after said resistor has been exposed to the atmosphere in said chamber and before said chamber is completely empty of oil.

6. A method as defined in claim 3 further including the step of producing a warning signal if oil does not flow out of said chamber within a predetermined time.

7. A system for signaling the presence of a first liquid in a second liquid, the first liquid having a lower vaporization point than the second liquid and being substantially immiscible in said second liquid, said system comprising a temperature sensitive element disposed in contact with said second liquid and possessing a characteristic which varies in proportion to changes of the temperature of said element, means for supplying heat energy to said element at a controllable rate to heat said element to a predetermined temperature between the vaporization points of said liquids, means for sensing the characteristic of said element and adjusting said supply means to raise said element back to said predetermined temperature when said element cools in response to said first liquid vaporizing adjacent said element, and means for producing an output signal which changes as a function of the average of the short term variations in the characteristic of said element.

8. A system as defined in claim 7 further including means responsive to said output signal for producing a warning signal when said output signal exceeds a predetermined threshold.

9. A system for signaling the presence of a predetermined concentration of water in a bath of oil, said system comprising a temperature sensitive resistor positioned in contact with said bath, means for supplying said resistor with electrical power sufficient to heat the resistor to a predetermined temperature above the vaporization point of water but below the vaporization point of said oil, means for producing a first signal which varies as a function of the drop in the resistance value of said resistor when the latter cools in response to the vaporization of water adjacent the resistor, means responsive to said signal for increasing the power supplied to said resistor sufficiently to raise said resistor back to substantially said predetermined temperature, and means for producing a warning signal when the time-average value of transient pulses in said first signal exceeds a predetermined threshold.

10. A system as defined in claim 9 in which said resistor is disposed within a chamber located in said bath and normally containing oil, and means for periodically causing at least some of the oil to flow from said chamber and for thereafter enabling oil from said bath to flow into said chamber.

11. A system as defined in claim 9 in which said resistor is disposed within a chamber immersed in and communicating with said bath, and means for alternately introducing pressurized gas into and venting said pressurized gas from said chamber thereby to cause oil to alternately flow out of and into said chamber, said last-mentioned means introducing pressurized gas into said chamber for a sufficient period of time to cause sufficient oil to flow from said chamber to leave said resistor exposed to said pressurized gas.

12. A system as defined in claim 11 in which said chamber includes an exhaust port for oil, said last-mentioned means introducing pressurized air into said chamber at periodic intervals, and means for terminating the flow of pressurized gas into said chamber after said resistor has been exposed to said pressurized gas and before said oil drops to the level of said exhaust port.

13. A system as defined in claim 12 in which said terminating means respond to changes in the resistance value of said resistor as oil flows out of said chamber.

14. A system as defined in claim 9 in which said resistor is disposed within a chamber located in said bath and having a port communicating with said bath and located below said resistor, means for introducing pressurized gas into said chamber at periodic intervals to cause oil to flow out of said chamber through said port, and means responsive to changes in the resistance value of said resistor for causing the introduction of pressurized air into said chamber to terminate and for causing said chamber to be vented when the oil in said chamber falls to a level between said port and the lower end of said resistor.

15. A system as defined in any of claims 10, 11, 12, 13 or 14 further including means for producing an alarm signal if oil does not flow out of said chamber within a predetermined period of time.

16. A system as defined in either of claims 10 or 11 further including an alarm normally operable to produce said warning signal, and means for disabling said alarm when oil is flowing out of and into said chamber.

17. A system as defined in claim 9 further including an alarm normally operable to produce said warning signal, and means independent of said pulses for triggering said alarm when the power supplied to said resistor exceeds a predetermined threshold.

18. A system as defined in claim 9 in which said resistor is coated with tetrafluoroethylene.

19. A system for signaling the presence of a predetermined concentration of water in a bath of oil, said system comprising a temperature sensitive resistor positioned in contact with said bath, a Wheatstone bridge, said resistor forming one of the resistance elements of said bridge, means for applying a voltage across the input terminals of said bridge to heat said resistor to a predetermined temperature above the vaporization point of water but below the vaporization point of said oil, means connected to the output terminals of said bridge for producing a first signal which changes as a function of the drop in the resistance value of said resistor when the latter is cooled by the vaporization of water adjacent said resistor, first means responsive to said first signal for increasing the voltage applied across the input terminals of said bridge to raise said resistor back to substantially said predetermined temperature, second means responsive to said first signal for averaging the transient variations in said first signal and for producing a secondsignal when the average of the variations exceeds a predetermined threshold, and warning means responsive to said second signal for producing an alarm signal.

20. A system as defined in claim 19 further including means for causing said warning means to produce said alarm signal when the voltage applied to the input terminals of said bridge exceeds a predetermined threshold.

21. A system for signaling the presence of a predetermined concentration of water in a bath of oil, said system comprising a temperature sensitive resistor positioned in contact with said bath, a Wheatstone bridge, said resistor forming one of the resistance elements of said bridge, means for applying a voltage across the input terminals of said bridge to heat said resistor to a predetermined temperature above the vaporization point of water but below the vaporization point of said oil, means connected to the output terminals of said bridge for producing a first signal which changes as a function of the drop in the resistance value of said resistor when the latter is cooled by the vaporization of water adjacent said resistor, first means responsive to said first signal for increasing the voltage applied across the input terminals of said bridge to raise said resistor back to substantially said predetermined temperature, second means responsive to said first signal for producing a second signal only when the magnitude of said first signal undergoes transient changes, third means responsive to said second signal for producing a third signal only when said second signal exceeds a predetermined magnitude, fourth means responsive to said third signal for producing a fourth signal which changes in magnitude as a function of the average of short term variations in said third signal, and fifth means responsive to said fourth signal for producing an alarm signal when the magnitude of said fourth signal exceeds a predetermined threshold.

22. A system for signaling the presence of a predetermined concentration of water in a bath of oil, said system comprising a temperature sensitive resistor positioned in contact with said bath, means for supplying said resistor with electrical power sufficient to heat the resistor to a predetermined temperature above the vaporization point of water but below the vaporization point of said oil, means for producing a first signal which varies as a function of the change in the resistance value of said resistor when the latter changes temperature in response to the vaporization of water adjacent the resistor, means responsive to said signal for varying the power supplied to said resistor sufficiently to restore said resistor substantially to said predetermined temperature, and means for producing a warning signal when the time-average value of transient pulses in said first signal exceeds a predetermined threshold.

* * * * *